US008277778B2

(12) United States Patent
Khamar et al.

(10) Patent No.: US 8,277,778 B2
(45) Date of Patent: Oct. 2, 2012

(54) VACCINE ADJUVANTS

(75) Inventors: Bakulesh Mafatlal Khamar, Ahmedabad (IN); Rajiv Indravadan Modi, Ahmedabad (IN); Indravadan Ambalal Modi, Ahmedabad (IN); Prasanta Kumar Ghosh, Ahmedabad (IN); Nirav Desai, Ahmedabad (IN)

(73) Assignee: Cadila Pharmaceuticals Ltd., Ahmedabad (IN)

( * ) Notice: Subject to any disclaimer, the term of this patent is extended or adjusted under 35 U.S.C. 154(b) by 0 days.

(21) Appl. No.: 13/242,909

(22) Filed: Sep. 23, 2011

(65) Prior Publication Data

US 2012/0014985 A1 Jan. 19, 2012

Related U.S. Application Data

(63) Continuation of application No. 10/583,731, filed as application No. PCT/IB2006/000978 on Apr. 21, 2006, now Pat. No. 8,048,434.

(30) Foreign Application Priority Data

Apr. 25, 2005 (IN) ........................... 505/MUM/2005

(51) Int. Cl.

| | |
|---|---|
| ***A61K 49/00*** | (2006.01) |
| ***A61K 39/04*** | (2006.01) |
| ***G01N 33/53*** | (2006.01) |

(52) U.S. Cl. .... 424/9.2; 424/9.1; 424/130.1; 424/184.1; 424/185.1; 424/234.1; 424/248.1; 435/4; 435/7.1; 435/7.2

(58) Field of Classification Search ................... 424/9.1, 424/9.2, 130.1, 184.1, 185.1, 234.1, 248.1; 435/4, 7.1, 7.2
See application file for complete search history.

(56) References Cited

FOREIGN PATENT DOCUMENTS

| | | |
|---|---|---|
| WO | WO02/056898 | 7/2002 |
| WO | WO03/049667 | 6/2003 |
| WO | WO03/075825 | 9/2003 |

OTHER PUBLICATIONS

Petrovsky N, Vaccine adjuvants: Current state and future trends; Immunology and Cell Biology (2004) 82, 488-496.

*Primary Examiner* — Rodney P. Swartz
(74) *Attorney, Agent, or Firm* — Burns & Levinson LLP

(57) ABSTRACT

The invention relates to a novel adjuvant *Mycobacterium* w and or its constituents and adjuvant containing composition, which contains antigen(s) with pharmaceutical acceptable carrier and its uses. *Mycobacterium* w and or its constituents when administered with antigen(s) to mammal results in enhanced immunogenicity of antigen. The enhanced immunogenicity manifests as humoral responses as well as cell mediated immunity. The adjuvant effect is seen with variety of antigens in various mammals irrespective of their immune status at the time of administration of *Mycobacterium* w and antigen containing composition. e.g. immune naïve or preimmunized status.

15 Claims, 12 Drawing Sheets

FIG: 1
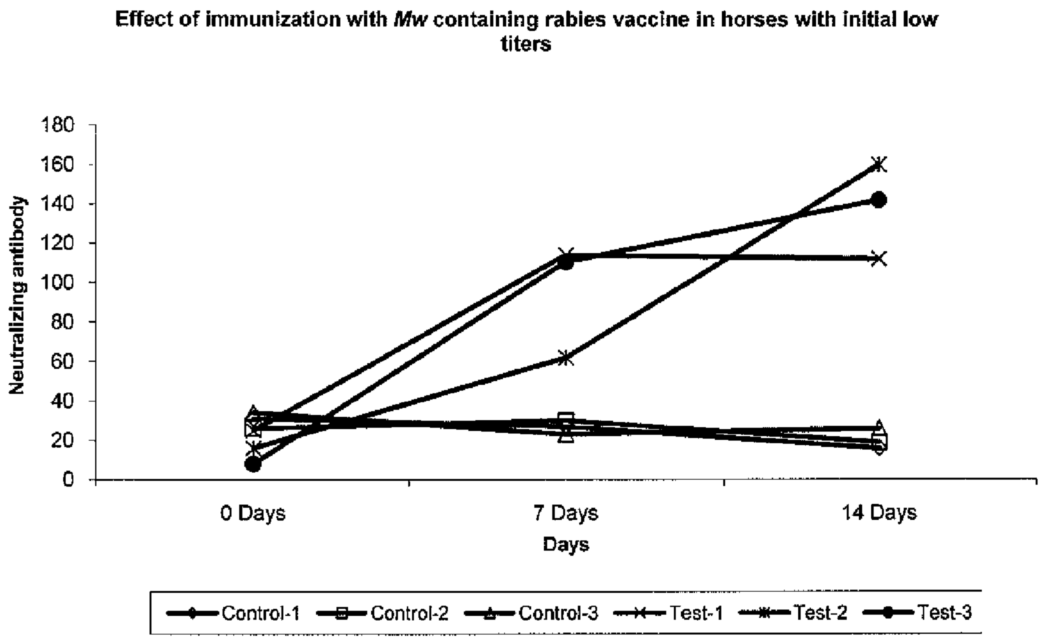

FIG: 2
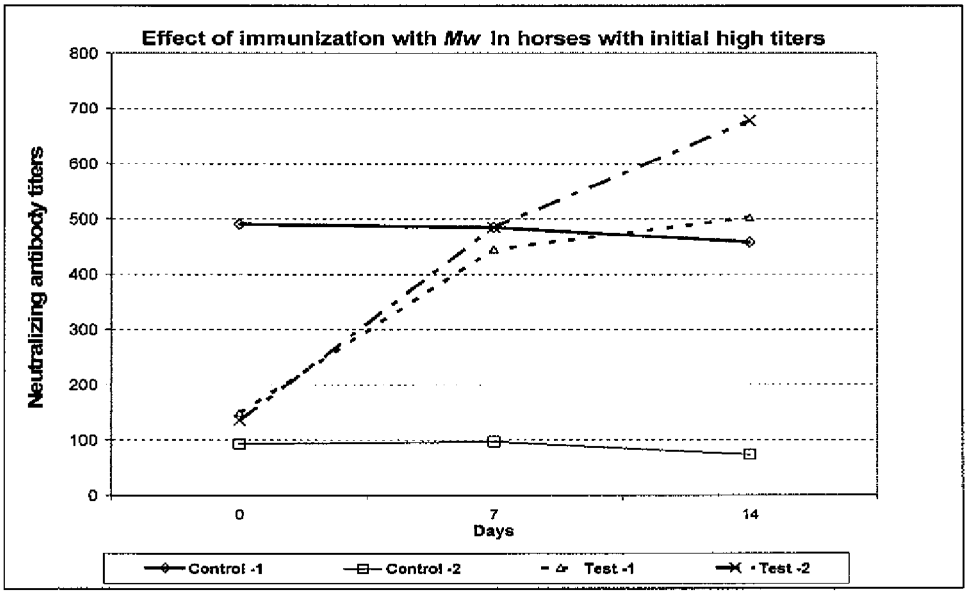

FIG: 3
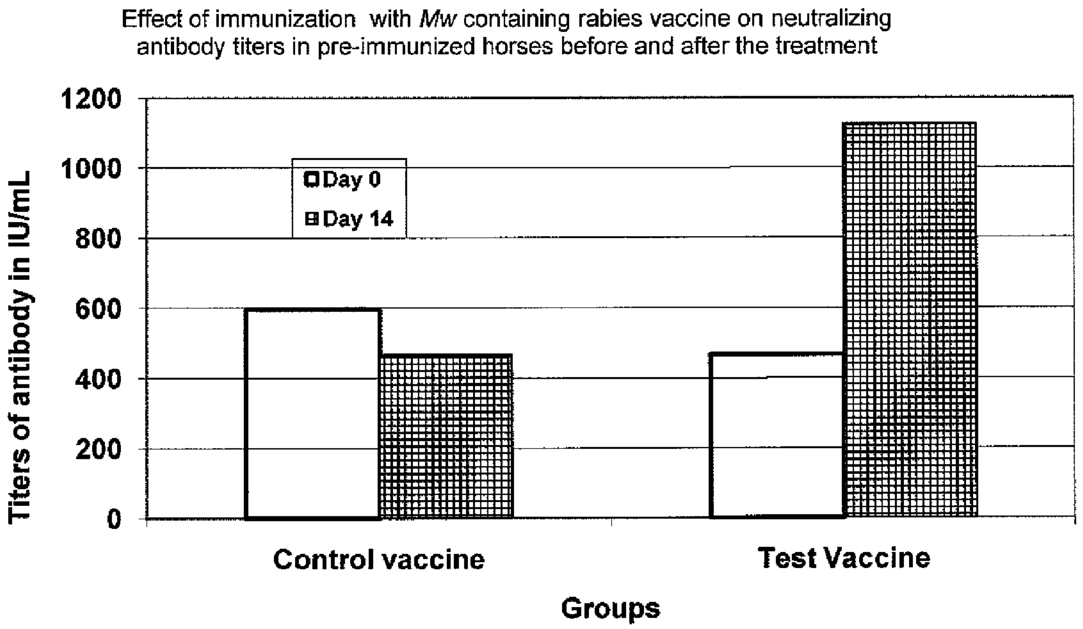

FIG: 4
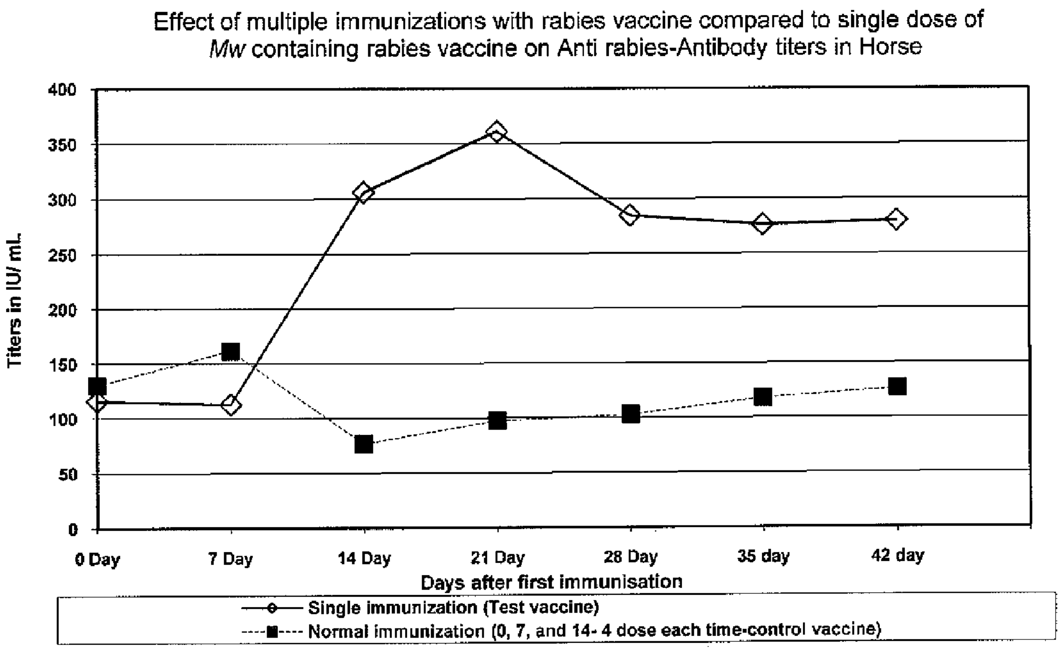

FIG: 5
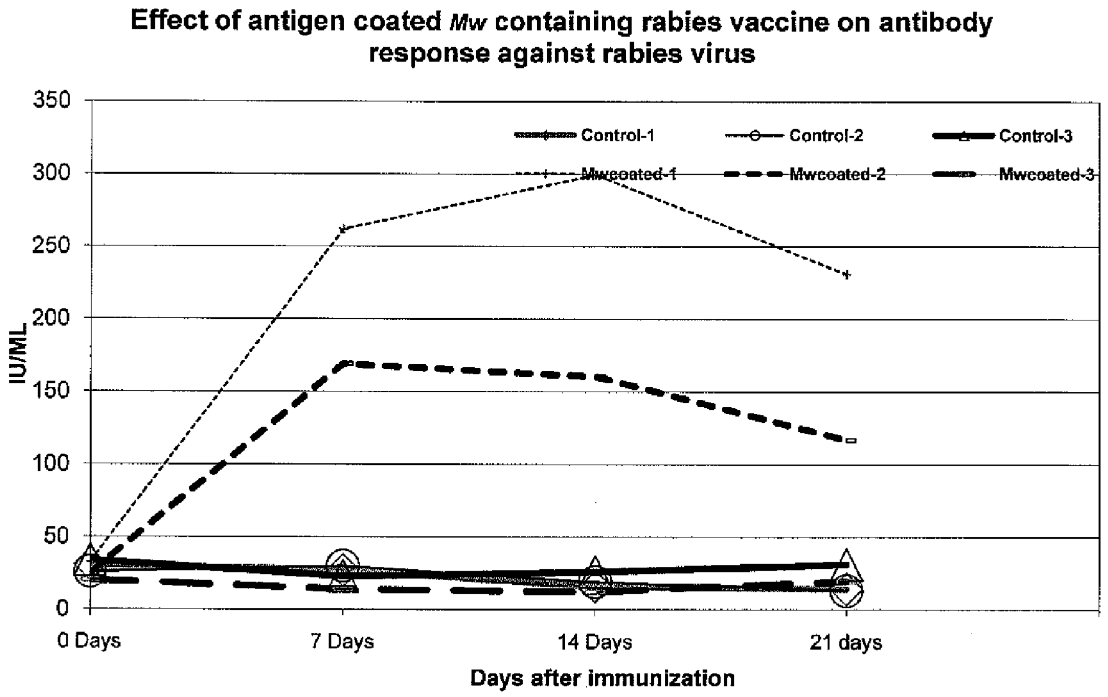

FIG: 6
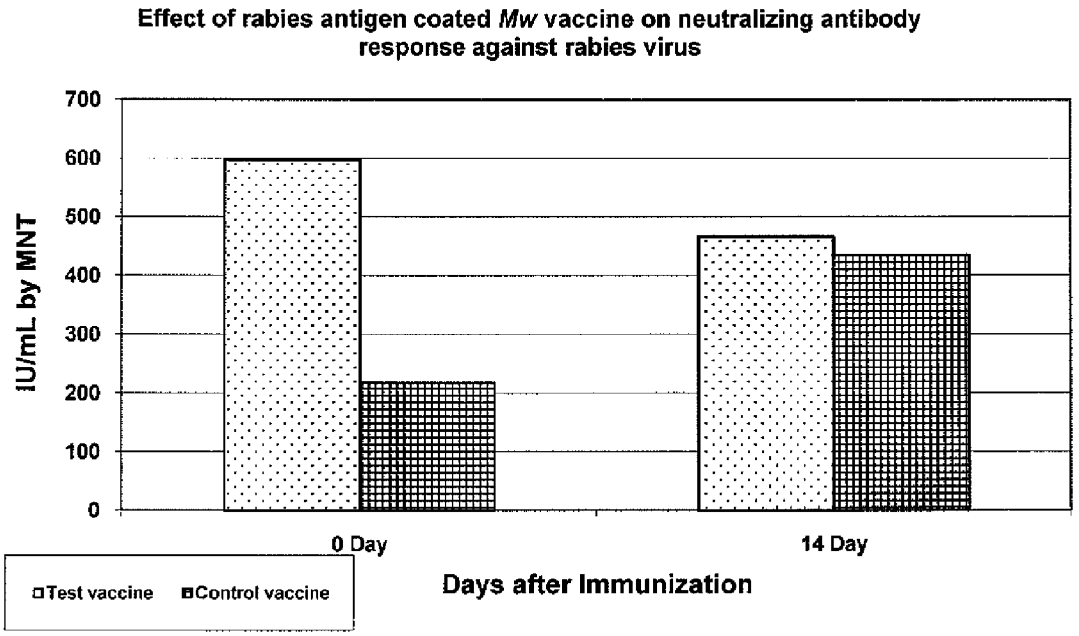

FIG: 7
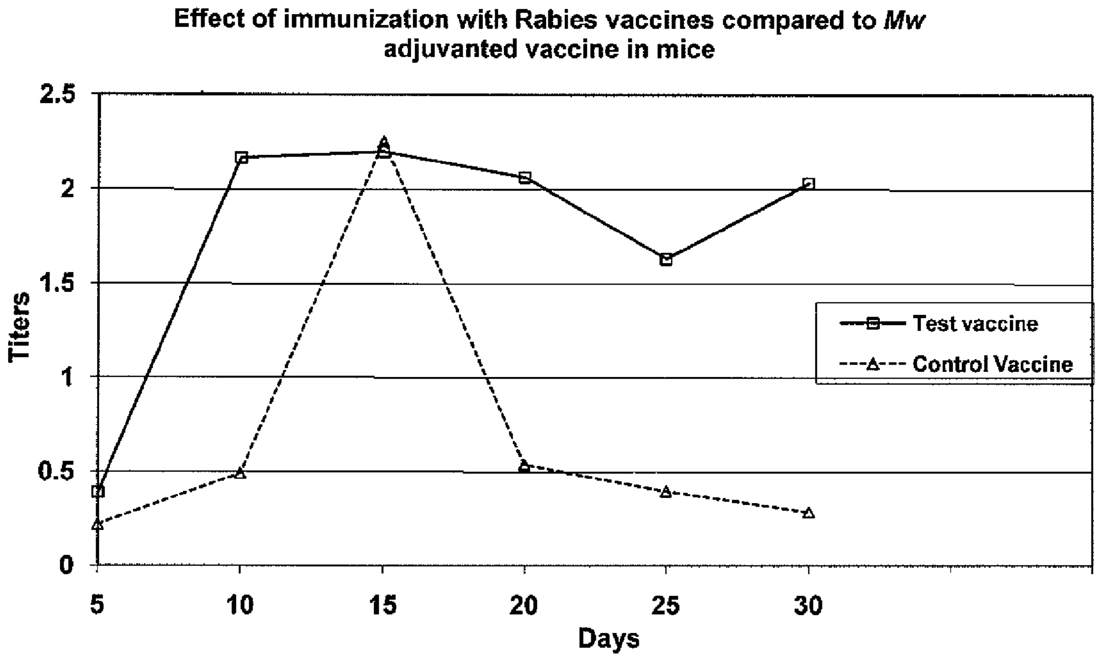

FIG: 8
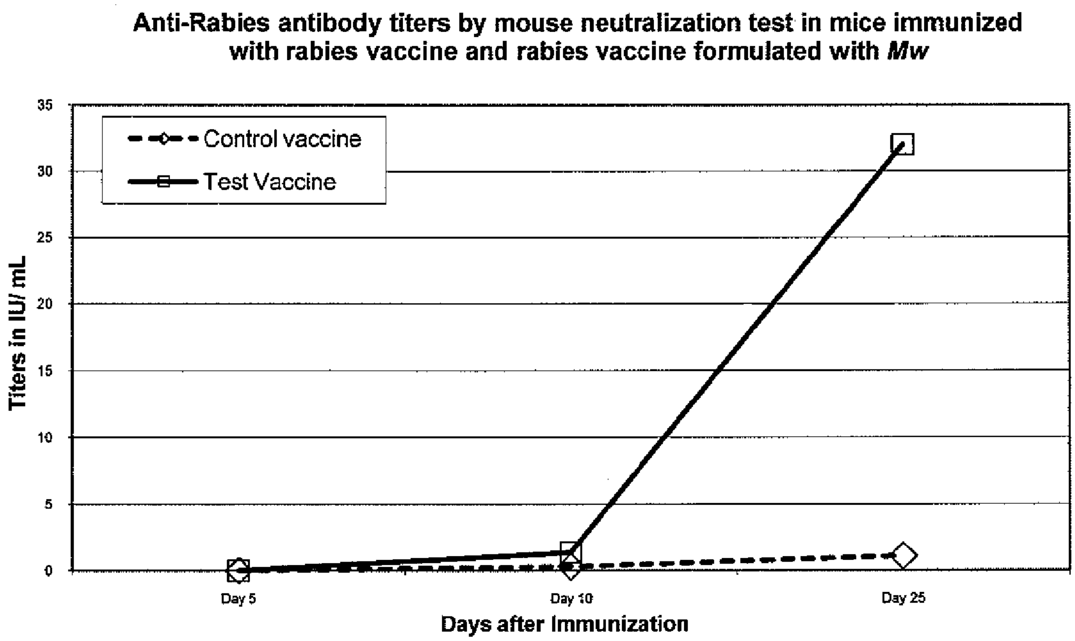

FIG: 9
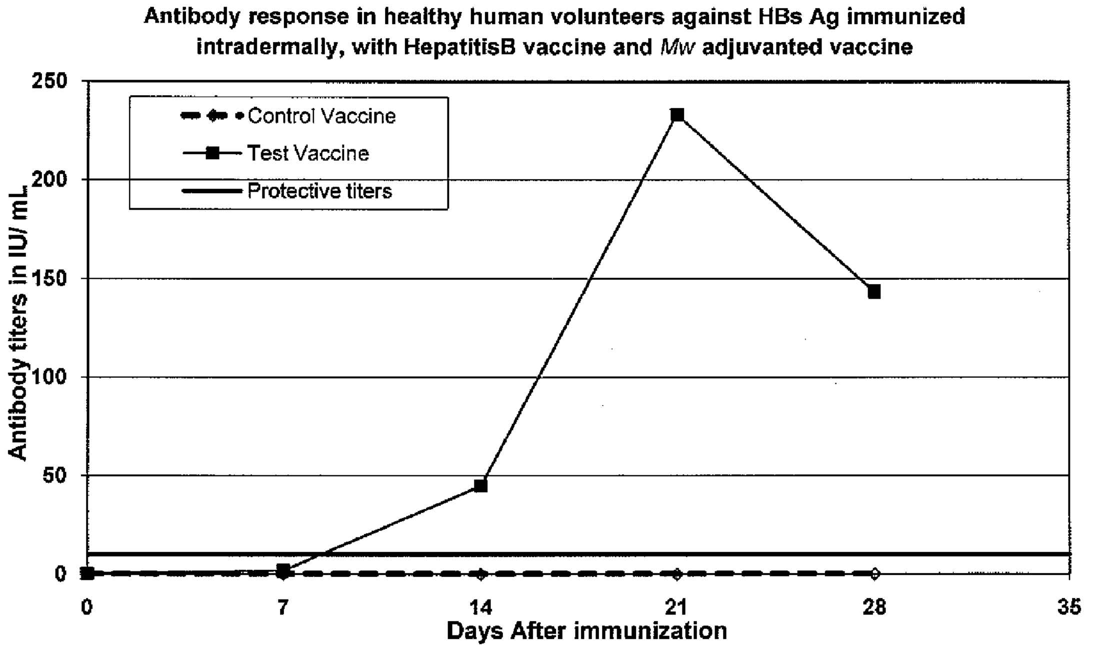

FIG: 10
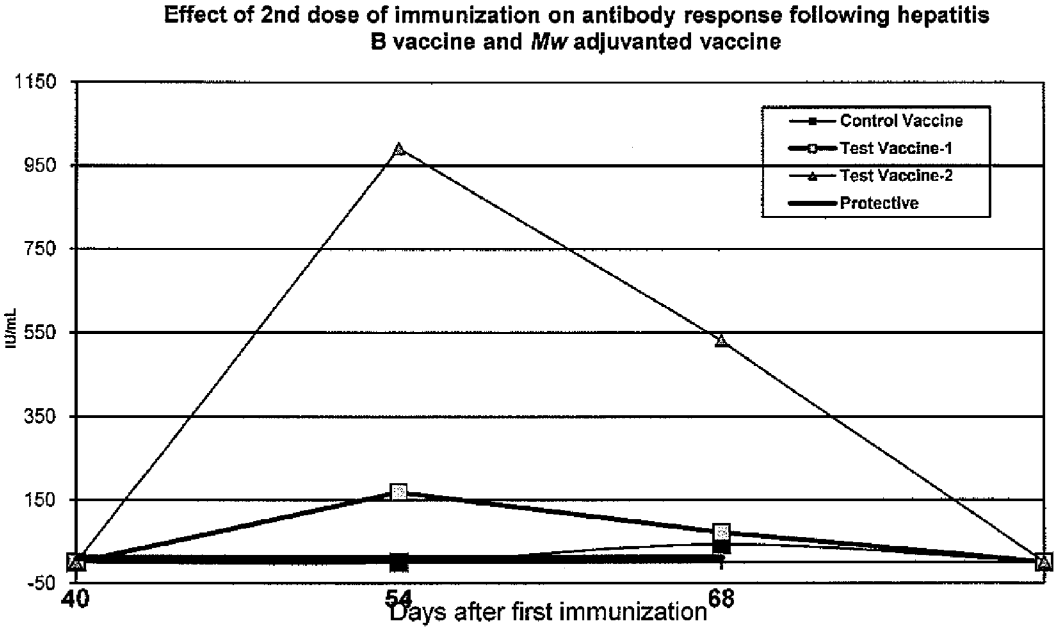

FIG: 11
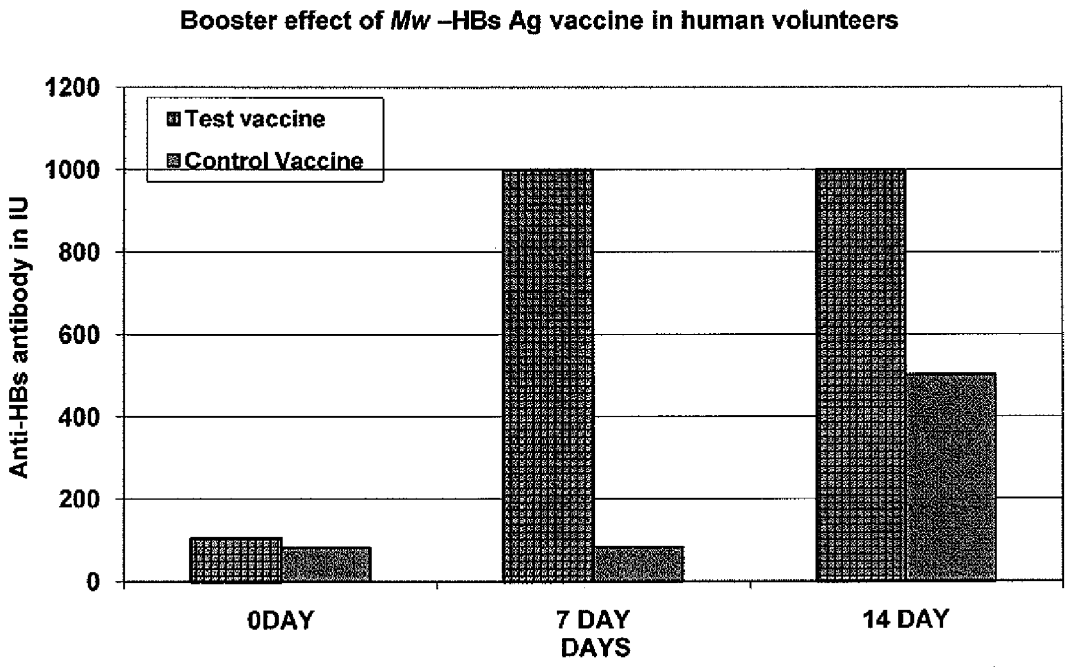

FIG: 12
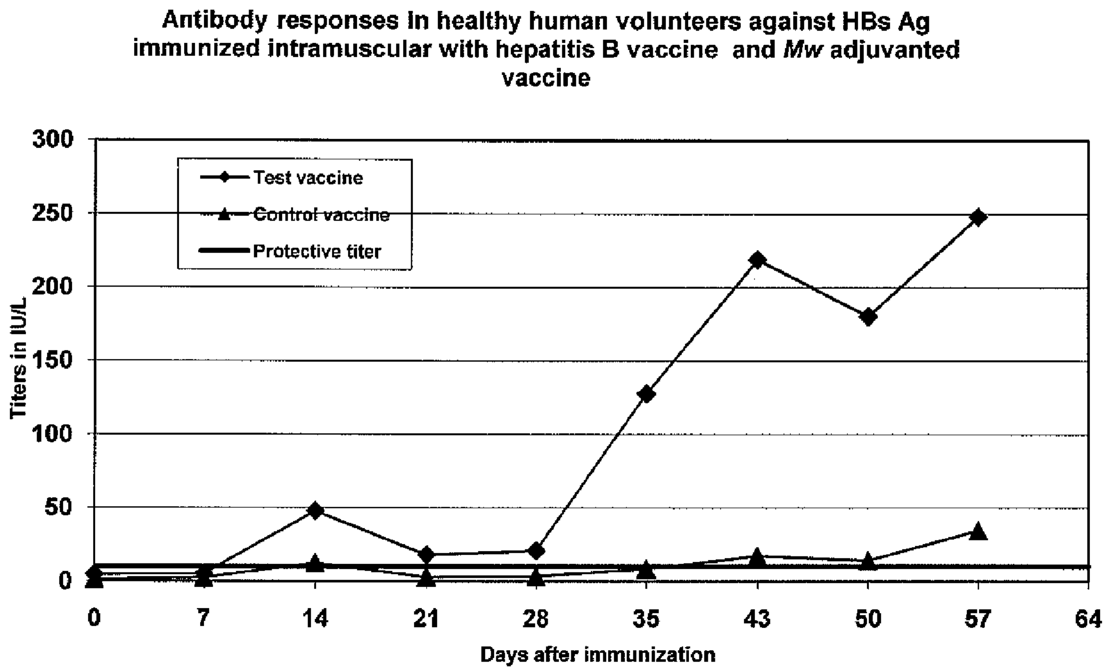

VACCINE ADJUVANTS

CROSS REFERENCE TO RELATED APPLICATION

This application is a Continuation patent application of U.S. Ser. No. 10/583,731, filed on Feb. 19, 2008, now granted U.S. Pat. No. 8,048,434, which is U.S. National Stage Application of International Application PCT/IB06/00978, filed Apr. 21, 2006, which claims the benefit of priority Indian Application No. 505/MUM/2005, filed Apr. 25, 2005, the entire contents of which are incorporated herein by reference.

FIELD OF INVENTION

The present invention pertains to novel adjuvants and compositions containing them with at least one antigen and methods for making and using the same.

BACKGROUND OF TILE INVENTION

In case of infection specific immune response is concerned with the recognition and ultimate disposal of the antigen/immunogen in a highly discriminatory fashion. Specific immune responses are mediated through two types of effectors mechanisms. One is mediated by antibody produced by lymphocytes (humoral response) and the other is mediated by specially sensitized lymphocytes themselves (cell mediated immunity). The humoral responses are mainly responsible for providing prophylaxis against disease (Prophylactic vaccine) while cell mediated immunity is mainly responsible for disease intervention (Therapeutic vaccine). Prophylactic vaccines are administered in anticipation of a disease. Therapeutic vaccines are administered in presence of an active disease.

The vaccine includes antigen (s) in a pharmaceutically acceptable carrier.

An antigen is a substance that stimulates an immune response.

Varieties of antigens are described in textbooks, monographs and articles. They include immunogens allergens, varieties of material including or derived from pathogens and non pathogen's like virus, bacteria, fungi, parasites, material derived from tumors or cells. The cells, organisms like virus, bacteria are also used in the intact form e.g. Polio, BCG etc. chemical composition of antigen is widely variable and include peptides of various kinds (like plain peptides, polypeptides, Lipopeptides etc.), polysaccharides, polysaccharide conjugates, lipids, glycolipids, carbohydrates, proteins, nucleic acids or antigen encoding nucleic acids.

They are categorized in varieties of ways. Some of them are described below.

Immunogen—Any substance that provokes the immune response when introduced into the body. An immunogen is always a macromolecule (protein, polysaccharide). Its ability to stimulate the immune reaction depends on its commonness to the host, molecular size, chemical composition and heterogeneity (e.g. similar to amino acids in a protein).

Allergen—An allergen is a substance that causes the allergic reaction. It can be ingested, inhaled, injected or comes into contact with skin.

Antigens can be classified in order of their origins.

Exogenous antigens-Exogenous antigens are antigens that have entered the body from the outside, for example by inhalation, ingestion, or injection.

Endogenous antigens—Endogenous antigens are antigens that have been generated within the cell, as a result of normal cell metabolism, or because of viral or intracellular bacterial infection. The fragments are then presented on the cell surface in the complex with class 1 histocompatibility molecules.

Tumor antigens-Tumor antigens are those antigens that are presented by the MHC I molecules on the surface of tumor cells. These antigens can sometimes be presented only by tumor cells and never by the normal ones. In this case, they arc called tumor-specific antigens and typically result from a tumor specific mutation. More common are antigens that are presented by tumor cells and normal cells, and they are called tumor-associated antigens. Cytotoxic T lymphocytes that recognize these antigens may be able to destroy the tumor cells before they proliferate or metastasize.

Tumor antigens can also be on the surface of the tumor in the form of, for example, a mutated receptor, in which case they will be recognized by B cells.

Pathogen Associated Antigens

Antigens are derived from pathogens like virus, bacteria, fungus, parasites e.g. rabies, hepatitis B, mump, measles, tetanus, diphtheria etc.

Antigens can be produced by recombinant technologies, extraction methods, chemical synthesis, fermentation etc. it can be in the form of a compound or an organism which is natural or genetically modified or a fraction of an organism, which is naturally occurring or genetically modified. Nucleic acids are increasingly being developed and identified as antigens as in DNA vaccines. Antigens can be administered in the form of naked antigens, or encapsulated, coated form, conjugated, mixed, coupled and/or formulated with adjuvant.

Most of the vaccines when applied alone do not produce an adequate immune stimulus, which is addressed by use of adjuvant e.g. alum in Hepatitis B vaccine to provide desired effect.

Directly increasing the number of cells involved,

Assuring efficient processing of antigen, prolonging the duration of antigen in immunized host, Or by increasing the antibody synthesis by antibody synthesizing cells.

Adjuvants are substances that enhance the immune response to antigens, but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

A wide range of adjuvants provokes potent immune responses to antigens. These include saponins complexed to membrane protein antigens (immune stimulating complexes), pluronic polymers with mineral oil, killed Mycobacteria in mineral oil, Freund's complete adjuvant, bacterial products, such as muramyl dipeptide (MDP) and lipopolysaccharide (LPS), as well as lipid A, and liposomes. To efficiently induce humoral immune response (HIR) and cell-mediated immunity (CMI), antigens are preferably emulsified in adjuvants.

Currently the only adjuvant widely used in humans has been alum. It contains aluminum salts (alum) and has been useful for some vaccines like hepatitis B, diphtheria, tetanus, toxoid etc., but not useful for others like rabies MMR, typhoid etc. It fails to induce cell-mediated immunity. Aluminum hydroxide and aluminum phosphate is collectively commonly referred to as alum. Reports indicate that alum failed to improve the effectiveness of whooping cough and typhoid vaccines and provided only a slight effect with adenovirus vaccines. Problems with alum include induction of granulomas at the injection site and lot-to-lot variation of alum preparations (U.S. Pat. No. 6,861,410).

Other adjuvants, such as saponin, Qui A, and the water-in-oil adjuvant, Freund's with killed tubercle bacilli (Freund's complete) or without bacilli (Freund's incomplete), have had limited use in humans due to their toxic effects; and, concerns have been raised as to undesirable effects in animals. Most adjuvant formulations have been described but most are never accepted for routine vaccines, mainly due to their toxicity and only few have been evaluated in humans Complete Freund's adjuvant (CFA) is a powerful immunostimulatory agent that has been successfully used with many antigens on an experimental basis. CFA includes three components: a mineral oil, an emulsifying agent, and killed *Mycobacterium tuberculosis*. Aqueous antigen solutions are mixed with these components to create a water-in-oil emulsion. Although effective as adjuvant, CFA causes severe side effects e.g. pain, abscess formation, fever etc. CFA, therefore, is not used in preparation of commercial vaccines.

Incomplete Freund's adjuvant (IFA) is similar to CFA but does not include the bacterial component. It is an oil in water emulsion. However, evidence indicates that both the oil and emulsifier used in IFA can cause tumors in mice.

Muramyl dipeptide (MDP) has been found to be the minimal unit of the mycobacterial cell wall complex that generates the adjuvant activity observed with CFA, e.g., Ellouz et al., Biochem. Biophys. Res. Commun. (1974) 59:1317. Several synthetic analogs of MDP have been generated that exhibit a wide range of adjuvant potency and side effects (Chedid et al., Prog. Allergy (1978) 25:63). Representative analogs of MDP include threonyl derivatives of MDP (Byars et al., Vaccine (1987) 5:223), n-butyl derivatives of MDP (Chedid et al., Infect. Immun. 35:417), and a lipophilic derivative of a muramyl tripeptide (Gisler et al., in Immunomodulations of Microbial Products and Related Synthetic Compounds (1981) Y. Yamamura and S. Kotani, eds., Excerpta Medica, Amsterdam, p. 167). One lipophilic derivative of MDP is N-acetylmuramyl-L-alanyl-D-isogluatrninyl-L-alanine-2-(1'-2'dipalmitoyl-sn-glycero-3-hydroxyphosphoryloxy)-ethylamine (MTP-PE). The MTP-PE itself is able to act as an emulsifying agent to generate stable oil-in-water emulsions. MTP-PE has been used in an emulsion of squalene with TWEEN 80, termed MTP-PE-LO (low oil), to deliver the herpes simplex virus gD antigen with effective results (Sanchez-Pescador et al., J. Immunol. (1988) 141:1720-1727), albeit with poor physical stability.

Synthetic polymers are evaluated as adjuvants. These include the homo- and copolymers of lactic and glycolic acid, which have been used to produce micro-spheres that encapsulate antigens (see Eldridge et al., Mol. Immunol. 28:287-294 (1993)).

Nonionic block copolymers are another synthetic adjuvant being evaluated. Adjuvant effects are investigated for low molecular weight copolymers in oil-based emulsions and for high molecular weight copolymers in aqueous formulations (Todd et al., Vaccine 15:564-570 (1997)).

In fact, the adjuvant effect of most experimental adjuvants has been associated with the adverse effects they elicit. Adjuvants that act as immunostimulators such as muramyl dipeptide, lipopolysaccaride, lipid A, monophosphoryl lipid A, and cytokines such as IL-2 and IL-12 can also cause systemic side-effects (general toxicity, pyrogenicity), limiting their use.

The adjuvants using whole cells like insect cells (*S. frugiperda*) are known (e.g., U.S. Pat. No. 6,224,882). The insects or the insect cells infected with some of the insect viruses/infectious agent or any other type of infection, also it is not yet possible to identify which insect/insect cell is infected and which not hence the use of these (i.e., insect/insect cell) can result in low production and a possible threat of transmission of disease to human (WHO report January 2005).

In an article published in Vaccine (1999) 17; 2446-2452, *Bacillus* of Calmette-Guerin (BCG) is used as adjuvant to rabies vaccination in mice. The experimental results show no improvement in serum neutralizing antibody titers in-group of mice immunized with BCG as adjuvant compared to plain vaccine.

U.S. Pat. No. 6,355,414 describes acemannan polysaccharide as adjuvant. U.S. Pat. No. 6,306,404 describes adjuvant & vaccine compositions of mono phosphoryl lipid A, sugar and optionally an amine-based surfactant. U.S. Pat. No. 6,231,859 describes saponin combination as adjuvant. Saponin adjuvants have high systemic toxicities, like haemolysis. The U.S. Pat. No. 6,060,068 describes interleukin-2 as adjuvant to vaccines. U.S. Pat. No. 6,355,256 describes QS-21 & IL-12 as adjuvants.

U.S. Pat. Nos. 6,103,697, 6,228,373 & 6,228,374 describes peptides as adjuvants. JP 11106351, JP 9268130 & AU 780054 describe oil adjuvants. But in all these adjuvants are not demonstrated with wide variety of antigens and mammals. Also the safety of these adjuvants is still to be confirmed.

Side effects of currently used adjuvants includes: (1) sensitization to tuberculin or any other antigen used in screening tests for infections; (2) presence in food animals of materials that cannot safely be ingested by humans; (3) inflammatory, granulomatous, necrotizing, or other unacceptable reactions at injection sites most notably as occurs with Freund's complete adjuvant; (4) pyrogenicity; (5) central nervous system effects and untoward behavioral effects; (6) impairment of growth; (7) arthritis; (8) increased vascular permeability and inflammatory reactions in the eye; (9) induction of undesired autoimmune responses and (10) immune suppression for adjuvant epitopes.

It is a long standing need of the industry to provide adjuvants that are free of above-mentioned side effects. Surprisingly, it is observed that *Mycobacterium* w and/or its constituents fulfill the requirement of adjuvant. Unlike Freund's adjuvant it provides immune stimulation in absence of emulsion. It is also not associated with systemic side effects like fever, body ache, muscle pain etc.

*Mycobacterium* w is a rapidly growing *Mycobacterium*. *Mycobacterium* w is a non-pathogenic, cultivable, atypical *Mycobacterium*, with biochemical properties and fast growth characteristics resembling those belonging to Runyons group IV class of Mycobacteria in its metabolic and growth properties but is not identical to those strains currently listed in this group. It is therefore thought that (Mw) is an entirely new strain. The species identity of Mw has been defined by polymerase chain reaction DNA sequence determination.

The *Mycobacterium* w has been found useful for treatment of Leprosy, Tuberculosis (Publication No: WO03075825-2003-09-18), and also for cancer treatment (Publication No: WO03049667-2003-06-19).

There is currently a need to have better adjuvants. The better adjuvants are needed in for improving efficacy of current vaccines like rabies wherein adjuvants like alum can not be used. They are needed to improve the efficacy of adjuvant containing current vaccines e.g. Hepatitis B vaccine containing alum. Better adjuvants are also needed to improve efficacy of various candidate vaccine so that they become effective and can be effective used e.g. CEA containing vaccines. The new adjuvants are also needed to provide novel vaccines for various new indications like vaccine for hepatic viral disease.

REFERENCES

1. Essential Immunology, Eight Edition
Ivan Roitt, Black well Scientific publication.
2. Vaccines, Third edition.
S. Plotkein W. Orenstein, W.B. Saunder's company
3. Vaccines Prospects & perspectives
Harminder sigh, rajesh Bhatia, forward publishing company, Delhi
4. Immunotherapy of cancer
Mary L. Disis, Humana press, Totowa, N.J., USA.
5. DNA vaccine
Douglas B. Lowrie, Robert a Whalen, Humana press, Totowa N.J., USA.
6. Handbook of cancer vaccines
Micheal A. Morse, Timothy M. Clay, H. Kiva Lyerly. Humana press Totowa N.J., USA.
7. Cellular Microbiology
Bian Henderson, Micheal Wilson, John wiley & sons.

SUMMARY OF INVENTION

Thus in accordance with the invention Mw preparations comprising of whole cell, and/or fraction there off individually or in combination, stimulates immune response against the formulated, mixed, or conjugated immunogen, for providing prophylactic and/or therapeutic vaccine.

The main object of invention is to provide adjuvant and adjuvant containing compositions that can stimulate the mammalian immune system against a wide variety of antigen (s). It is another object of invention to provide *Mycobacterium* w or its constituents as an adjuvant.

It is yet another objective to provide compositions containing *Mycobacterium* w or its constituents as an adjuvants and antigen (s) in a pharmaceutically acceptable carrier.

It is yet another objective to provide heat killed *Mycobacterium* was an adjuvant.

It is yet another objective to provide adjuvant and adjuvant to containing compositions made of whole *Mycobacterium* w and or its constituents.

It is yet another objective of present invention to provide a method for inducing or enhancing immunogenicity of an antigen in a mammal. The method includes administering to the mammal a vaccine composition that includes the antigen and a vaccine adjuvant composition that includes an effective immunopotentiatory amount of Mw and/or its constituents.

It is yet another objective to provide adjuvant that stimulates immune system which when mixed formulated, conjugated, primed or any other type of formulation with specific antigen/immunogen.

It is yet another objective to provide adjuvant composition wherein antigen (s) is selected from peptides, polypeptides, cells, cell extracts, polysaccharides, polysaccharide conjugates, lipids, glycolipids, carbohydrates, proteins, viruses, viral extracts, and antigen encoding nucleic acids.

It is yet another objective to provide adjuvant and adjuvant containing compositions which comprises of *Mycobacterium.*

It is yet another objective to provide adjuvant and adjuvant containing compositions that stimulates the cell mediated immune response.

It is yet another objective to provide adjuvant that stimulates the immune system faster, better and for a longer period.

DETAILED DESCRIPTION

List of Figures and their Description

FIG. 1. Effect of immunization with Mw containing rabies vaccine in horses with initial high titers.

FIG. 2. Effect of immunization with Mw containing rabies vaccine in horses with initial low titers.

FIG. 3. Effect of immunization with Mw containing rabies vaccine on neutralizing antibody titers in pre-immunized horses before and after the treatment.

FIG. 4. Effect of multiple immunizations with rabies vaccine compared to single dose of Mw containing rabies vaccine on Anti rabies-Antibody titers in Horse FIG. 5. Effect of rabies antigen coated Mw vaccine on antibody response against rabies virus in horse.

FIG. 6 Effect of antigen coated Mw vaccine on neutralizing antibody response against rabies virus in horse.

FIG. 7 Effect of immunization with Rabies vaccines compared to Mw adjuvanted vaccine in mice.

FIG. 8. Anti-Rabies antibody titers by mouse neutralization test in mice immunized with rabies vaccine and rabies vaccine formulated with Mw.

FIG. 9. Antibody response in healthy human volunteers against HBs Ag immunized intradermally, with Hepatitis B vaccine and Mw adjuvanted vaccine.

FIG. 10. Effect of $2^{nd}$ dose of immunization on Antibody response following hepatitis B vaccine and Mw adjuvanted vaccine.

FIG. 11. Booster effect of Mw-HBs Ag vaccine in human volunteers.

FIG. 12 Antibody responses in healthy human volunteers immunized intramuscular with hepatitis B vaccine and Mw adjuvant.

FOLLOWING EXAMPLE DESCRIBED THE PROCESS OF OBTAINING CONSTITUENTS/FRACTIONS OF *MYCOBACTERIUM* W

Method of Growing *Mycobacterium* w

1. Culturing of *Mycobacterium* w a) Preparation of Culture Medium

*Mycobacterium* w is cultured on solid medium more particularly on LJ medium or more particularly in liquid medium like Middlebrook medium or sautn's Liquid Medium.

Middlebrook medium is enriched for better yield. It can be preferably enriched by addition of glucose, bactopeptone, and bovine serum albumin and additives there on. They are used in several ratios, preferably used in ratio of 20:30:2.

The enrichment medium is added to the Middlebrook medium in several different ratio from 15:1 to 25:1 more preferably in the ratio 20:1.

b) Bioreactor Preparation.

a. Preparation of Vessel

The inner contact parts of the vessel (Joints, Mechanical seals, o-Ring/gasket, Grooves etc.) are properly cleaned to avoid any contamination. The vessel is filled up with 0.1N NaOH and left as such for 24 hrs to remove pyrogenic materials and other contaminants. The vessel is then cleaned first with acidified water, then three times with distilled water before preparing medium.

b. Sterilization of Bioreactor

The bioreactor containing nine liters distilled water is sterilized with live steam (Indirect/direct). Similarly the bioreactor is sterilized once more with Middlebrook medium. The other addition bottles, inlet/outlet air filters etc. are autoclaved twice at 131.6° C. for 15 minutes. Before use these are dried at 50° C. in an oven.

c. Environmental Parameters i. Temperature: 37±0.5° C.

ii. pH: 6.7 to 6.8 initially

2. Harvesting and Concentrating

It is typically done at the end of $6^{th}$ day after culturing under aseptic condition but can be harvested at any time between 6 hrs to 15 days. The concentration of cells (pelletization) is done by centrifugation.

3. Washing of Cells

The pellet so obtained is washed for minimum three times with normal saline. It can be washed with or without detergent containing fluid, which is preferably isotonic.

4. Adding pharmaceutically acceptable carrier.

Pyrogen free normal saline is added to pallet. Any other pyrogen free fluid can be used as pharmaceutical carrier. The carrier is added in amount so as to get desired concentration of active material in final form.

5. Adding Preservative

To keep the product free from other contaminating bacteria for its self life, preservative is added. Preferred preservative is thiomersal in final concentration of 0.005% v/v to 0.1% w/v more preferably 0.01% w/v.

6. Terminal Sterilization

Terminal sterilization can be done by various physical methods like application of heat or ionizing radiation or sterile filtration.

Heat can be in the form of dry heat or moist heat. It can also be in the form of boiling or pasteurization. Ionizing radiation can be ultraviolet or gamma rays or microwave or any other form of ionizing radiation.

It is preferable to autoclave the final product. This can be done before or after final packaging.

7. Quality Control a) The material is evaluated for purity and sterility.

b) The organisms are checked for acid fastness and gram staining.

c) Inactivation test: This is done by culturing the product on LJ medium to find out any living organism.

d) Pathogenicity and/or contamination with pathogen

The cultured organisms are infected to Balb/c mice. None of the mice should die and all should remain healthy and gain weight. There should not be any macroscopic or microscopic lesions seen in liver, lung, spleen, or any other organs when animals are sacrificed up to eight weeks following treatment.

e) Biochemical Test f) The organism is subjected to following tests i. Urease ii. Tween 80 hydrolysis iii. Niacin Test iv. Nitrate reduction test The organism gives negative results in urease, tween 80 hydrolysis and niacin test. It is positive by nitrate reduction test

Following Examples Illustrates the Processes Used for Obtaining Constituents of *Mycobacterium* w the Scope of Invention is not Limited by them 1. Cell Disruption The cell disruption can be done by way of sonication or use of high pressure fractionometer or by application of osmotic pressure gradient. The disrupted cells were washed with physiological saline and repelleted by centrifugation.

1. Solvent Extraction

Any organic solvent like alcohols, halogenated hydrocarbons, acetone, phenol, isopropyl alcohol, acetic acid, hexane and/or aromatic compound individually or in any combination thereof can do the solvent extraction.

2. Enzymatic extraction.

The enzymatic extraction can he done by enzymes, which can digest cell wall/membranes. They are typically proteolytic and lytic in nature. Enzyme lysozymes, liticase and pronase are the preferred enzymes.

The cell constituents/fractions of *Mycobacterium* w were used alone in place of *Mycobacterium* w organisms and/or they were added to the product containing *Mycobacterium* w. Addition of cell constituents results in improved efficacy of the product.

Methods to Illustrate the Manufacture of Composition Containing *Mycobacterium* w and or its Constituents as an Adjuvant The Mw as whole cell or fraction were formulated by mixing of Mw in an isotonic solution, fraction of Mw formulated in appropriate buffer and/or conjugated with an antigen or immunogen chemical coupling agents like aldehydes, carbodiamides, anhydrides and any such compound.

Following examples demonstrate the invention and are not limiting for purpose of invention.

EXAMPLE 1

*Mycobacterium* w cells were grown as mentioned above in Middlebrook media and were killed by autoclaving at 121.6° C. under steam pressure of 15 Psi. The cells were suspended in sterile pyrogen free normal saline. The cells were checked for sterility and purity. The cells were diluted to a final concentration of $10^9$ cells per mL. The cells were mixed with the antigen, in one of the example the antigen is HBs ag. These mixtures are used as vaccine where Mw acts as adjuvant.

EXAMPLE 2

The heat killed Mw cells and/or its constituents were activated by 1-ethyl-3-(3-dimethylaminopropyl)carbodiimide hydrochloride (Sigma) and were coated with antigen, by mixing the activated cells with antigen. The molar ratio of antigen to cell used was in the range of 1:2 to 1:100 preferably in the ratio of 1:50. This composition was used for immunization where Mw and/or its constituents act as adjuvant.

Following Examples Illustrate the Adjuvant Effect

Following example describes the Method of using *Mycobacterium* w and its constituents/fractions as adjuvant. Following experiments demonstrate the adjuvant effect of present invention and they do not limit scope of invention.

A. Adjuvant effect as per present invention in preimmunized horses receiving rabies vaccine for purpose of evaluating effect compositions containing *Mycobacterium* w and/or its constituents were formulated and evaluated for effect on antibody titer. All single injections of control vaccine (Rabipur) as well as test vaccine contained inactivated rabies virus more than or equal to 2.5 IU/ml. They were given in a different dosage (no. of injections) or interval as mentioned. Antibody titers were measured by ELISA method and were further evaluated with mice neutralizing antibody test.

EXAMPLE 1

Immunization of Horse Against Rabies Using Mw Adjuvant:

Horses immunized with rabies vaccine (Rabipur) were re-immunized by administering rabies vaccine (Rabipur) reconstituted with water or with *Mycobacterium* w containing normal saline. Each horse received 1.0 ml of reconstituted Rabipur intramuscularly in two doses of 0.5 ml each over each shoulder. The blood was withdrawn at the beginning (zero day) and at the intervals of seven and fourteen days following re-immunization. The blood was analyzed for rabies antibody titer using ELISA against reference standard. The blood samples were also evaluated for neutralizing rabies antibodies using mouse neutralizing antibody test.

FIG. 1 shows the effect of both vaccines on serum antibody levels in horses, three in each group, having very low initial antibody titer. The vaccine alone does not raise the antibody titer while vaccine with Mw is capable of raising the titer to significant higher level on day 7. This increases further on day 14.

FIG. 2 Shows the effect of both vaccines on serum antibody levels in horses, two in each group, having high initial antibody titer. The vaccine alone does not raise the antibody titer while vaccine with Mw is capable of raising the titer to significant higher level on day 7. This increases further on day 14.

When neutralizing antibodies were evaluated using mouse-neutralizing test, it was observed that there was no effect on neutralizing antibody levels in control group (receiving rabies vaccine alone) but there was significant improvement in a group receiving the vaccine with *Mycobacterium* w. (test group) There was more than two fold rise in neutralizing antibody titer on day 14 compared to base level in test group (FIG. 3).

EXAMPLE 2

The test groups received rabies vaccine reconstituted with Mw while the control group received only rabies vaccine. The test group was immunized on day 0 with a single injection of vaccine as described earlier. The control group received four injections each of rabies vaccine on day 0, 7 and 14. (Total of 12)

The results as shown in FIG. 4, the test group shows better immune response compared to the control. The antibody response in test group is achieved with lesser amount of antigen compared to the control group.

EXAMPLE 3

Test vaccine as per invention was evaluated in same horses who received four injection of standard rabies vaccine a times at the interval of 4 weeks (16 injections total) prior to it. All received only one injection of test vaccine which contained same load of antigen as contained in single injection of rabies vaccine.

The antibody titer generated in horses with test vaccine is higher than or equal to whatever is produced in same horse with four injections of control vaccine given every week for a total of 16 injections. The antibody titer is also reached between 2 and 3 week in test group compared to five weeks in test group.

EXAMPLE 4

A group of five horses (Test Group) were immunized with rabies vaccine and the other group (Control Group) was immunized with the rabies antigen coated Mw. Each horse received 1 ml of vaccine intramuscularly. The horses were bled at an interval of every 7 days for the period of one month.

The titers of specific antibodies were measured by ELISA and MNT.

The titers of antibody in test group were significantly higher then in the control group horses from day 7 onwards as shown in FIGS. 5 & 6.

EXAMPLE 5

Immunization of Mice Against Rabies

Mice were administered 0.2 ml of rabies vaccine (Rabipur) reconstituted in water (control) or reconstituted with *Mycobacterium* w (Mw) containing normal saline. In each group thirty mice were immunized. From each group 5,10,15,20,25 and on 30th day five mice for each group were bled to obtain sera.

The vaccine was administered 0.2 ml intradermally divided into two injections of 0.1 ml each, over each side of back. The antibody titer was evaluated subsequent to vaccine administration at the interval of 5 days. The antibody titer was measured by ELISA (FIG. 7). The findings suggest that addition of *Mycobacterium* w achieves higher antibody titter in comparison to control. It achieves such high titer very early. The peak value is achieved on day 10 in Mw group compared to day 15 in control group. On day 10 value achieved by Mw group is more than twice that of control group.

In a control group after reaching the peak on day 15 it declines rapidly and value achieved on day 20 is less than half of that achieved on day 15 & is not detectable on day 25 & 30. In Mw group, value on day 20 is more than twice compared to control group, which is maintained on day 25 & day 30.

The samples were checked for specific isotypes of IgG.

These antibodies were having a major component of IgG2a isotype antibody, as isotyped by IgG Isotyping kit (SIGMA).

EXAMPLE 6

Mouse Neutralizing Antibody Body Against Rabies.

Serum obtained on day 5, day 10, & day 25 from example five above was used to detect mouse neutralizing antibodies by inoculating into brain of mice along with live rabies virus (Mouse neutralizing test).

On day 5, in both the groups the neutralizing antibody titer were non detectable. On day 10 Mw group contained 1.35 IU/ml while control group contained 0.2975 of neutralizing antibodies. Even after the $25^{th}$ day the specific neutralizing antibody titers were significantly also higher in-group with Mw as adjuvant then in control group. The titer of Mw group was 32 IU/mL while the control group just achieved the protective titer of 1.09 IU/mL.

This clearly shows the faster and specific induction of neutralizing antibody response to protective titers in 10 days in Mw group as indicated in the table 2 and FIG. 8.

TABLE 2

| Effect of immunization with Immuvac Mw in mice | | |
|---|---|---|
| | Rabies control vaccine | Rabies vaccine Mw |
| Day 5 | Not detectable | Not Detectable |
| Day 10 | 0.2975 | 1.35 |
| Day 25 | 1.09 | 32.00 |

B: Adjuvant Effect as Per Present Invention in Healthy Human Volunteers Receiving Hepatitis B Vaccine.

Compositions as per present inventions were prepared to have Hepatitis B antigen (Test vaccine) and compared with Hepatitis-B vaccine (Engerix-B). Both (Test vaccine as well as control vaccine) contained 20 microgram/ml of Hepatitis-B antigen. Antibody titers were measured using commercially available ELISA kit.

EXAMPLE 1

Effect of Single Intradermal Dose

After informed consent two groups of 15 human subjects male adults each were randomly selected and immunized by intradermal route. With a single shot of either Hepatitis B vaccine (Engerix B) alone or as incorporating Mw the antigen of hepatitis B used was 2 mcg. Serum samples were analyzed for the antibody titer on week 1, 2, 3, and 4 post-immunization. The results indicate that all of the volunteers in control group failed to rise against hepatitis B. The 10 IU/mL is the protective level. On the other hand, group containing the vaccine incorporating Mw achieved significantly high titer (FIG. 9), more than the requisite levels of protective antibody titer.

EXAMPLE 2

Effect of Second Intradermal Dose

On $35^{th}$ day after first immunization, individuals with no response received a second dose of immunization with test or control vaccine intradermally.

The antibody responses after second dose were determined at every seven days. The anti-HBs antibodies in test group were significantly increased compared to the titers in control group as shown in FIG. 10. In control group only one of six individuals receiving second dose of control vaccine had rise in antibody titer.

EXAMPLE 3

Booster Effect of Single Dose of Intradermal Hepatitis B Vaccine

Two individuals in with protective titers on day 0 received either a test vaccine or a control vaccine.

After immunization with respective vaccines, their antibody titers were improved in both.

EXAMPLE 4

Effect of Intramuscular Administration

In another example, 46 human male adult subjects, each were randomly selected and immunized intramuscular with a single shot of either Hepatitis B vaccine (control vaccine (Engerix 13)) alone or formulated with Mw (test vaccine). 15 volunteers received the control vaccine, while 31 volunteers were immunized with test vaccine. The antigen of hepatitis B used was 20 mcG. Serum samples were analyzed for the antibody titer on week 1, 2, 3, 4, 6, and 7 post-immunization. The results indicate that all of the volunteers in control group failed to rise against hepatitis B. The 10 IU/mL is the protective level. On the other hand, group containing the vaccine incorporating Mw achieved significantly high titer (FIG. 12). All achieved more than the requisite levels of protective antibody titer with a single injection. All received a second injection of control of test vaccine on day 28. There was a significant rise in antibody titer in test group (FIG. 12). The rise was also seen in control group but was not so remarkable.

EXAMPLE 5

Adjuvant Effect of Mw for Cell Mediated Immune Response Against HBs Ag in Mice A group of five mice (test group) were immunized with Hepatitis B vaccine (Engerix B) mixed with Mw and another group of five mice (control group) received appropriately diluted Hepatitis B vaccine. The immunization was performed sub-cutaneously.

Each mouse received 2 microgram of HBs antigen. The test group received the same dose of 2-microgram antigen formulated in Mw cells.

After 15 days the mice were bled and PBMC were isolated. The isolated cells were cultured in complete RPMI media with 10% FBS and 1 μG/mL concanavalin A as mutagen at 37° C. and 7% $CO_2$ for 72 Hrs and stimulated with HBs antigen.

After 72 hrs the cells were harvested and are subjected to ELISPOT for IFN-γ, IL-2. The results were obtained with ELISPOT reader.

The results showed that the cells producing IFN-γ and IL-2 were significantly higher in test group compared to control group.

C: Adjuvant Effect as Per Present Invention to Demonstrate Effect on Cell Mediated Immunity when Disease Antigens are Incorporated into the Composition.

EXAMPLE 1

Adjuvant Effect of Mw for Cell Mediated Immune Response Against Cancer Antigen Ca—19.9 in Mice A group of five mice were immunized with CA—19.9 (Sigma) alone (control group) or with a composition as per present invention. All mice were immunized with subcutaneous injections of 0.2 mL on lower back.

Each mouse received 10 IU of CA—19.9 antigen. The test group received the same dose of 10 IU antigen formulated in Mw cells.

After 15 days the mice were bleed and PBMC were isolated. The isolated cells were cultured in complete RPMI media with 10% FBS and 1 μG/mL concanavalin A as mutagen at 37° C. and 7% $CO_2$ for 72 Hrs and stimulated with CA—19.9 antigen.

After 72 hrs the cells were harvested and are subjected to ELISPOT for IFN-γ and IL-2.

The results showed that number of cells secreting IFN-γ and IL-2 were significantly more in test group compared to control group.

EXAMPLE 2

Adjuvant Effect of Mw for Cell Mediated Immune Response Against Pneumococcal Antigen in Mice A group of five mice were immunized with pneumococcal antigen alone (control group) or with a composition as per present invention. All mice were immunized with subcutaneous injections of 0.2 mL on lower back containing 0.1 mL of pneumococcal antigen.

After 15 days the mice were bled and PBMC were isolated. The isolated cells were cultured in complete RPMI media with 10% FBS and 1 μG/mL concanavalin A as mutagen at 37° C. and 7% $CO_2$ for 72 hrs and stimulated with pneumococcal antigen.

After 72 hrs the cells were harvested and are subjected to ELISPOT for IFN-γ, IL-2 and IL-12.

The results showed that number of cells producing IFN-γ were less in the control group then the test group. The IL-2 response was observed only in test group.IL-12 secreting cells were significantly higher in test group.

EXAMPLE 3

Adjuvant Effect of Mw for Cell Mediated Immune Response Against Influenza Virus Antigen in Mice A group of five mice were immunized with Influenza vaccine (Vaxigrip) mixed with Mw and another group of five mice received appropriately diluted influenza vaccine. All mice were immunized with subcutaneous injections of 0.2 mL on lower back.

Each mouse received 0.10 ml of influenza vaccine. The test group received the same dose of antigen formulated in Mw cells.

After 15 days the mice were bled and PBMC were isolated. The isolated cells were stimulated in complete RPMI media with 10% FBS and 1 μG/mL concanavalin A as mutagen at 37° C. and 7% $CO_2$ for 72 Hrs and stimulated with influenza vaccine.

After 72 hrs the cells were harvested and are subjected to ELISPOT for IFN-γ, IL-2 and IL-12.

The results showed that number of cells producing IFN-γ, IL-2 and IL-12 in the test group were higher then the control group. The effect was maximum for IL-12 followed by IL-2 & IFN γ.

EXAMPLE 4

Adjuvant Effect of for Cell Mediated Immune Response Against *Salmonella typhi* Vi Antigen in Mice A group of five mice (test group) were immunized with *Salmonella typhi* Vi antigen mixed with Mw and the other group of five mice (control group) received appropriately diluted *Salmonella typhi* Vi antigen. All mice were immunized with subcutaneous injections of 0.2 mL on lower back.

Each mouse received 0.1 ml *Salmonella typhi* Vi antigen. The test group received the same dose of antigen formulated in Mw cells.

After 15 days the mice were bled and PBMC were isolated. The isolated cells were cultured in complete RPMI media with 10% FBS and 1 μG/mL concanavalin A as mutagen at 37° C. and 7% $CO_2$ for 72 hrs and stimulated with *Salmonella typhi* Vi antigen. After 72 hrs the cells were harvested and are subjected to ELISPOT for IFN-γ, IL-2 and IL-12.

The results showed that in the test group had more number of cells producing IFN-γ, IL-2 and IL-12 then control group. The effect was maximum with 1-12 followed by IL-2 & IFN-γ.

EXAMPLE 5

Adjuvant Effect of Mw for Cell Mediated Immune Response Against Hepatitis A Antigen in Mice A group of five mice (test group) were immunized with hepatitis A antigen (Havrix) mixed with Mw and the other group of five mice (Control group) received appropriately diluted hepatitis A antigen. All mice were immunized with subcutaneous injections of 0.2 ml on lower back.

Each mouse received 140 U of hepatitis A antigen. The test group received the same dose of 140 U antigen formulated in Mw cells.

After 15 days the mice were bled and PBMC were isolated. The isolated cells were cultured in complete RPMI media with 10% FBS and 1 μG/mL concanavalin A as mutagen at 37° C. and 7% $CO_2$ for 72 hrs and stimulated with hepatitis A antigen.

After 72 hrs the cells were harvested and are subjected to ELISPOT for IFN-γ and IL-2. The results showed that in the test group number of cells producing IL-2 and IFN-γ were significantly higher then the control group.

The above examples demonstrate the working of present invention when variety of different kinds of antigens were incorporated. For some of them like rabies, typhoid, pneumococcal, currently there are no adjuvants incorporated into commercially available preparation due to the fact that the current adjuvants do not provide desired effect. It also demonstrate added adjuvant effect when combined with known adjuvant like alum. Thus adjuvant of present invention appears to be universal with better efficacy.

These examples clearly shows that the Mw when used as adjuvant can stimulate specific cell mediated immune response.

The results as shown in pre-immunized horses the single injections of the test vaccines elicits the antibody titer higher than the horses immunized with multiple injections of rabies vaccine.

The examples with human volunteers and horses also indicates that the protective titers can be achieved by single immunization dose with test vaccine in 7 to 10 days while the similar titers can be achieved with conventional vaccine after one month or more with multiple injections.

The examples above show that the subject for the immune stimulation by present invention can be any mammal including small mice, large mammal like horse and human. The net response is identical in all the animals. The test compositions stimulates Cell Mediated Immunity is evident from above examples.

Mw when used along with rabies vaccine achieves a higher peak antibody level earlier, reducing time for first appearance of antibody, compared to control group & maintains it for prolonged period.

Example above also shows the faster and specific induction of neutralizing antibody response to protective titers in 10 days in Mw group as indicated in the table 2 and FIG. 7

None of the animals and human volunteers demonstrated any signs of local or generalized toxicity & vaccine was well tolerated. Identical results are also obtained when fractions/constituents of *Mycobacterium* w or whole Mw is used.

Mw and/or its constituents there off can stimulate immune response in human against a specific antigen without any adverse effect. Also the route of immunization does not matter to the immune response when administered with Mw as adjuvant.

This is indicative of the potential of Mw for eliciting enhanced and sustained humoral immune response for all antigens. As demonstrated by all the above examples the said adjuvant, Mw shall be used as whole or its constituents there off to enhance the stimulation of immune response against practically any antigen/immunogen.

We claim:

1. A method for generating an immune response against an antigen by administration of a pharmaceutical composition comprising said antigen and *Mycobacterium w* and/or constituents thereof as an adjuvant.

2. The method as claimed in claim 1 wherein the antigen(s) is a cell, a virus, a bacterium, a fungus, a parasite, a constituent thereof or a combination thereof.

3. The method as claimed in claim 1 wherein the antigen is selected from the group consisting of one or more peptides, one or more polypeptides, one or more cells, one or more cell extracts, one or more polysaccharides, one or more polysaccharide conjugates, one or more lipids, one or more glycolipids, one or more carbohydrates, one or more proteins, one or more viruses, one or more viral extracts, and one or more nucleic acid-based antigen encoded in nucleic acids.

4. The method as claimed in claim 1 wherein the antigen is an allergen.

5. The method as claimed in claim 1 wherein the antigen is a tumor associated antigen.

6. The method as claimed in claim 1 wherein the antigen is a tumor specific antigen.

7. The method as claimed in claim 1, wherein the immune response generated is a humoral immune response.

8. The method as claimed in claim 1, wherein the immune response generated is a cell mediated immune response.

9. The method as claimed in claim 1 wherein the administration of said *Mycobacterium w* and/or constituents thereof to a mammal induces or enhances immunogenicity of said antigen(s).

10. The method as claimed in claim 1 is used for the treatment of a disease.

11. The method as claimed in claim 10 wherein the treatment comprises generating immune response against a disease specific antigen.

12. The method as claimed in claim 1 wherein the administration of said *Mycobacterium w* and/or constituents thereof induces or enhances immunogenicity of antigen(s) resulting in decreased morbidity & mortality associated with a disease.

13. The method as claimed in claim 1 wherein administration of said *Mycobacterium w* and/or constituents thereof when combined with another therapy in a diseased mammal induces or enhances immunogenicity of antigen(s) and results in decreased morbidity & mortality associated with disease.

14. The method of claim 1 wherein said pharmaceutical composition is administered by a parenteral route.

15. The method of claim 1 wherein the pharmaceutical composition is administered by intramuscular, subcutaneous, or intradermal route.

* * * * *